United States Patent
Kaiser et al.

(10) Patent No.: US 11,043,295 B2
(45) Date of Patent: Jun. 22, 2021

(54) METHOD AND PROVIDING UNIT FOR PROVIDING A VIRTUAL TOMOGRAPHIC STROKE FOLLOW-UP EXAMINATION IMAGE

(71) Applicant: Siemens Healthcare GmbH, Erlangen (DE)

(72) Inventors: Nico Kaiser, Erlangen (DE); Sebastian Schmidt, Weisendorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 61 days.

(21) Appl. No.: 16/540,436

(22) Filed: Aug. 14, 2019

(65) Prior Publication Data

US 2020/0066393 A1    Feb. 27, 2020

(30) Foreign Application Priority Data

Aug. 24, 2018    (DE) ...................... 10 2018 214 325.0

(51) Int. Cl.
*G16H 30/20*    (2018.01)
*G16H 50/30*    (2018.01)
(Continued)

(52) U.S. Cl.
CPC ............. *G16H 30/20* (2018.01); *G06N 20/00* (2019.01); *G06T 7/0012* (2013.01); *G16H 50/20* (2018.01);
(Continued)

(58) Field of Classification Search
CPC ........ G16H 30/20; G16H 50/30; G16H 50/20; G16H 30/40; G06N 20/00; G06N 3/0454; G06N 3/0445; G06N 3/0472; G06N 3/08; G06N 20/10; G06T 2207/10081–10088; G06T 2207/30104; G06T 2207/20084; G06T 2207/10096; G06T 2207/10072–10076; G06T 7/0012–0016;
(Continued)

(56) References Cited

U.S. PATENT DOCUMENTS 9,892,361 B2 *   2/2018  Nguyen .................... A61B 5/00
9,898,824 B2 *   2/2018  Betting ..................... G06T 7/11
(Continued)

OTHER PUBLICATIONS

Grech, Reuben et al. "Outcome Prediction in Acute Stroke Patients Considered for Endovascular Treatment: a Novel Tool" Interventional Neuroradiology, vol. 20, pp. 312-324, 2014 // Doi: 10.15274/INR-2014-10029.
(Continued)

*Primary Examiner* — Michael S Osinski
(74) *Attorney, Agent, or Firm* — Harness, Dickey & Pierce, P.L.C.

(57) ABSTRACT

A method is disclosed for providing a virtual tomographic stroke follow-up examination image. In an embodiment, the method includes: receiving a sequence of temporally successive tomographic perfusion imaging data sets of a region for examination; calculating the virtual tomographic stroke follow-up examination image of the region for examination by applying a trained machine learning algorithm to the sequence of temporally successive tomographic perfusion imaging data sets received; and providing the virtual tomographic stroke follow-up examination image calculated.

20 Claims, 5 Drawing Sheets

(51) Int. Cl.
*G06N 20/00* (2019.01)
*G06T 7/00* (2017.01)
*G16H 50/20* (2018.01)

(52) U.S. Cl.
CPC ... *G16H 50/30* (2018.01); *G06T 2207/10081* (2013.01)

(58) Field of Classification Search
CPC ............. G06T 7/11; G06T 2207/20081; G06T 2207/30016; G06T 11/003; A61B 5/055; A61B 6/032; A61B 6/504; A61B 6/037; A61B 6/486
See application file for complete search history.

(56) References Cited

U.S. PATENT DOCUMENTS

| | | | | |
|---|---|---|---|---|
| 10,867,384 | B2* | 12/2020 | Song | G06N 3/0454 |
| 2009/0129642 | A1* | 5/2009 | Matsumoto | G06T 5/50 382/128 |
| 2009/0326360 | A1* | 12/2009 | Baillet | G06T 7/0012 600/410 |
| 2010/0004909 | A1* | 1/2010 | Nitz | G01R 33/54 703/4 |
| 2011/0009732 | A1* | 1/2011 | Sugiyama | G01R 33/4806 600/410 |
| 2011/0257510 | A1* | 10/2011 | Weiss | G01R 33/56341 600/411 |
| 2012/0201441 | A1* | 8/2012 | De Oliveira | G01R 33/56509 382/131 |
| 2013/0303885 | A1* | 11/2013 | Hoshino | G01R 33/56366 600/419 |
| 2015/0071520 | A1* | 3/2015 | Takemoto | A61B 6/486 382/132 |
| 2015/0087980 | A1* | 3/2015 | Yao | G01S 7/52038 600/440 |
| 2015/0379706 | A1* | 12/2015 | Leonhardt | G01R 33/56366 382/131 |
| 2016/0018501 | A1* | 1/2016 | Kimura | G01R 33/56308 324/322 |
| 2016/0128795 | A1* | 5/2016 | Kozuka | G16H 30/20 715/771 |
| 2016/0232661 | A1* | 8/2016 | Ohishi | G06T 11/003 |
| 2016/0314589 | A1* | 10/2016 | Nagao | G16H 30/20 |
| 2016/0367200 | A1* | 12/2016 | Voskrebenzev | A61B 5/055 |
| 2017/0071479 | A1* | 3/2017 | Kano | A61B 5/107 |
| 2017/0091929 | A1* | 3/2017 | Hofmann | A61B 6/032 |
| 2017/0091930 | A1* | 3/2017 | Kozuka | H04N 1/00442 |
| 2017/0140551 | A1* | 5/2017 | Bauer | G06K 9/6256 |
| 2017/0178319 | A1* | 6/2017 | Sugiura | G01R 33/5602 |
| 2017/0325755 | A1* | 11/2017 | Grass | A61B 5/7285 |
| 2018/0028156 | A1* | 2/2018 | Matsunaga | A61B 8/4254 |
| 2018/0101968 | A1* | 4/2018 | Bannasch | G06T 15/08 |
| 2018/0180697 | A1* | 6/2018 | Samson-Himmelstjerna | A61B 5/0263 |
| 2018/0322617 | A1* | 11/2018 | Carmi | G06T 5/50 |
| 2019/0033419 | A1* | 1/2019 | Golay | G01R 33/58 |
| 2019/0053780 | A1* | 2/2019 | Song | A61B 8/06 |
| 2019/0287674 | A1* | 9/2019 | Nitta | G06K 9/4628 |
| 2019/0328355 | A1* | 10/2019 | Calderon Agudo | A61B 8/0808 |
| 2019/0336033 | A1* | 11/2019 | Takeshima | G06N 20/00 |
| 2020/0202551 | A1* | 6/2020 | Ciofolo-Veit | A61B 8/463 |
| 2020/0315455 | A1* | 10/2020 | Lee | A61B 5/7282 |
| 2021/0042885 | A1* | 2/2021 | Yabusaki | G06T 7/0012 |

OTHER PUBLICATIONS

Yu, Yannan et al. "Prediction of Hemorrhagic Transformation Severity in Acute Stroke From Source Perfusion MRI" IIEEE Transactions on Biomedical Engineering 2018, vol. 65, No. 9, Sep. 2018 (Date of publication: Dec. 20, 2017) // DOI: 10.1109/TBME.2017.2783241.

Nielsen, Anne et al. "Prediction of Tissue Outcome and Assessment of Treatment Effect in Acute Ischemic Stroke Using Deep Learning" Stroke; vol. 49; No. 6; pp. 1394-1401, 2018 // DOI: 10.1161/STROKEAHA.117.019740.

Hachaj, Tomasz et al. "Neural Network Approach for Identification of Selected Brain Perfusion Abnormalities" 6th International Conference on Innovative Mobile and Internet Services in Ubiquitous Computing, pp. 52-57, 2012 // DOI 10.1109/IMIS.2012.15.

Cuenod, C. A. et al. "Perfusion and vascular permeability: Basic concepts and measurement in DCE-CT and DCE-MRI" Diagnostic and Interventional Imaging, vol. 94, pp. 1187-1204, 2013 // http://dx.doi.org/10.1016/j.diii.2013.10.010.

Wu, Ona et al. "Characterizing physiological heterogeneity of infarction risk in acute human ischaemic stroke using MRI" Brain; vol. 129; No. 9; pp. 2384-2393, 2006 // DOI: 10.1093/brain/awl183.

Graham, Dillon et al. "Convolutional Drift Networks for Video Classification" IEEE International Conference on Rebooting Computing (ICRC), Nov. 2017, DOI: 10.1109/ICRC.2017.8123647 // arXiv:1711.01201v1 [cs.CV].

Rekik, Islem et al. "Medical image analysis methods in MR/CT-imaged acute-subacute ischemic stroke lesion: Segmentation, prediction and insights into dynamic evolution simulation models. A critical appraisal" NeuroImage: Clinical, vol. 1, 2012 // DOI: 10.1016/j.nicl.2012.10.003.

Flottmann, Fabian et al. "CT-perfusion stroke imaging: a threshold free probabilistic approach to predict infarct volume compared to traditional ischemic thresholds" Nature, Scientific Reports, vol. 7, No. 6679, Jul. 2017 // DOI:10.1038/s41598-017-06882-w.

Hachaj, Tomasz et al. "Application of neural networks in detection of abnormal brain perfusion regions" Neurocomputing, vol. 122, pp. 33-42, 2013 // http://dx.doi.org/10.1016/j.neucom.2013.04.030.

Roberts, Caleb et al. "Comparative Study into the Robustness of Compartmental Modeling and Model-Free Analysis in DCE-MRI Studies" Journal of Magnetic Resonance Imaging, vol. 23, pp. 554-563, 2006 // DOI 10.1002/jmri.20529.

German Office Action for German Application No. 102018214325, dated May 6, 2019.

* cited by examiner

METHOD AND PROVIDING UNIT FOR PROVIDING A VIRTUAL TOMOGRAPHIC STROKE FOLLOW-UP EXAMINATION IMAGE

PRIORITY STATEMENT

The present application hereby claims priority under 35 U.S.C. § 119 to German patent application number DE 102018214325.0 filed Aug. 24, 2018, the entire contents of each of which are hereby incorporated herein by reference.

FIELD

Embodiments of the invention generally relate to a method for providing a virtual tomographic stroke follow-up examination image, a providing unit, a computer program product and a computer-readable storage medium.

BACKGROUND

Dynamic contrast enhanced (DCE) imaging, or perfusion imaging, for use in computed tomography (CT), also called DCE-CT or perfusion CT, is an imaging method by means of which physiological properties, in particular the perfusion of a tissue, can be analyzed. Among other things, DCE imaging is helpful in diagnosing strokes, in which parts of the brain suffer oxygen deficiency because of poor blood supply, and from which irreversible damage can arise.

In order to identify regions that are at risk, a sequence of images is captured while a contrast agent is administered, and the change over time in the attenuation values for individual pixels or particular regions is determined. On the basis of these curves, perfusion properties can be calculated, and these are then plotted on a CT image or magnetic resonance (MRI) image, typically with color coding, in so-called perfusion maps ([1]).

Calculation of the parameters is usually based on complex mathematical models that represent an approximation of physiological processes in the tissue. In this context, there are many different methods, to be selected depending on the pathology and the tissue. Since they are approximations, inaccuracies in the model may result in erroneous results. Moreover, with these methods curves have to be adapted, on the basis of the measured data and the respective models, which in turn may give rise to errors and requires considerable processing time. It is frequently also necessary to consider the artery in segmented form in order to determine the AIF (arterial input function). This too may vary depending on the method or user, and so have an adverse effect on standardization and hence also on the comparability of the values.

Different physiological models give different parameters to be interpreted. Ultimately, however, most approaches to stroke imaging have the objective of making a prediction of where in the brain irreversible damage is a threat and thus where an intervention is required. The different mathematical models for calculating the perfusion parameters take into account different component parts of the microcirculation in the tissue. Some of these models are not easy to understand and calculate. It is also difficult to keep an overview of how the results of the different variants are to be interpreted.

Moreover, there are various methods of analyzing DCE images automatically, for example nonparametric perfusion analysis and automatic perfusion analysis using perfusion maps.

In nonparametric perfusion analysis (also called "non-pk perfusion analysis" or "model free perfusion analysis"), the curve characteristics are grouped into particular classes by means of machine learning in order to be able to identify pathologies or anomalies. This method is uncoupled from the parametric mathematical models. However, its results are difficult to interpret, and only the time characteristics of the curves are analyzed, without taking into account the image information. An example of nonparametric analysis in DCE-MRI can be found in [2].

In automatic perfusion analysis using perfusion maps, algorithms of machine learning are applied to perfusion maps that have already been drawn up, in order to identify tissue that is at risk. In most cases, however, the features are identified and extracted manually, and the algorithm is only used for classification. In many devices currently in use, for this purpose it is even simply the case that only a threshold value is used for the perfusion maps. However, threshold-based methods are susceptible to noise, and include no information on local blood supply to the neighboring regions.

Neural network approaches also exist, for example for predicting the infarct volume in perfusion maps. However, these are dependent on the perfusion parameters that were used as the basis for calculating the perfusion maps ([3], [4], [5]). There are also methods that predict the possible success of a particular treatment of the stroke ([6]). A review paper of various methods for image processing for stroke diagnosis in MRI/CT can be found in [7].

SUMMARY

At least one embodiment of the invention enables prediction of the effects of a stroke on the tissue to be improved. Further advantageous embodiments of the invention are taken into account in the claims.

At least one embodiment of the invention relates to a method for providing a virtual tomographic stroke follow-up examination image, wherein the method includes:

receiving a sequence of temporally successive tomographic perfusion imaging data sets of a region for examination, for example by means of a receiving interface, calculating the virtual tomographic stroke follow-up examination image of the region for examination by applying a trained machine learning algorithm to the sequence of temporally successive tomographic perfusion imaging data sets, for example by means of a processor unit, and providing the virtual tomographic stroke follow-up examination image, for example by means of a providing interface.

At least one embodiment of the invention relates to a method for providing a virtual tomographic stroke follow-up examination image, the method comprising:

receiving a sequence of temporally successive tomographic perfusion imaging data sets of a region for examination;

calculating the virtual tomographic stroke follow-up examination image of the region for examination by applying a trained machine learning algorithm to the sequence of temporally successive tomographic perfusion imaging data sets received; and providing the virtual tomographic stroke follow-up examination image calculated.

Further, at least one embodiment of the invention relates to a providing unit for providing a virtual tomographic stroke follow-up examination image, wherein the providing unit includes:

a receiving interface, intended for receiving a sequence of temporally successive tomographic perfusion imaging data sets of a region for examination, a processor unit, intended for calculating the virtual tomographic stroke follow-up examination image of the region for examination by applying a trained machine learning algorithm to the sequence of temporally successive tomographic perfusion imaging data sets, and a providing interface, intended for providing the virtual tomographic stroke follow-up examination image.

Still further, at least one embodiment of the invention relates to a providing unit for providing a virtual tomographic stroke follow-up examination image, comprising:

a receiving interface, to receive a sequence of temporally successive tomographic perfusion imaging data sets of a region for examination;

a processor, to calculate the virtual tomographic stroke follow-up examination image of the region for examination by applying a trained machine learning algorithm to the sequence of temporally successive tomographic perfusion imaging data sets received; and a providing interface, to provide the virtual tomographic stroke follow-up examination image calculated Further, at least one embodiment of the invention relates to a computer program product having a computer program that may be loaded directly into a storage unit of a providing unit, having program sections in order to perform all the steps of a method according to one of the disclosed embodiments when the program sections are executed by the providing unit.

Further, at least one embodiment of the invention relates to a non-transitory computer-readable storage medium on which program sections that are readable and executable by a providing unit are stored in order to perform all the steps of the method according to one of the disclosed embodiments when the program sections are executed by the providing unit.

Further, at least one embodiment of the invention relates to a non-transitory computer program product, storing a computer program, directly loadable into a storage unit of a providing unit, including program sections to perform the method of an embodiment when the program sections are executed by the providing unit.

Further, at least one embodiment of the invention relates to a non-transitory computer-readable storage medium storing program sections, readable and executable by a providing unit, to perform the method of an embodiment when the program sections are executed by the providing unit.

BRIEF DESCRIPTION OF THE DRAWINGS

The invention will be explained below by example embodiments, with reference to the attached figures. Representation in the figures is schematic, highly simplified and not necessarily to scale.

In the figures.

DETAILED DESCRIPTION OF THE EXAMPLE EMBODIMENTS

Figure 1:
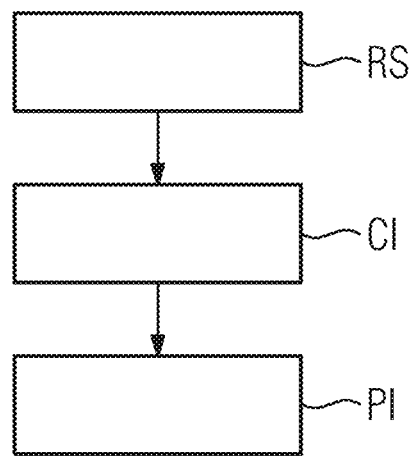
FIG. 1 shows a flow chart for a method for providing a virtual tomographic stroke follow-up examination image.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for providing a virtual tomographic stroke follow-up examination image, wherein the method includes:

receiving a sequence of temporally successive tomographic perfusion imaging data sets of a region for examination, for example by means of a receiving interface, calculating the virtual tomographic stroke follow-up examination image of the region for examination by applying a trained machine learning algorithm to the sequence of temporally successive tomographic perfusion imaging data sets, for example by means of a processor unit, and providing the virtual tomographic stroke follow-up examination image, for example by means of a providing interface.

The region for examination may be in particular a region for examination in a patient. The region for examination may be for example a brain or a brain region of a patient.

Data, in particular the sequence of temporally successive tomographic perfusion imaging data sets of a region for examination, may be received by receiving a signal that carries the data, and/or by reading the data off from a computer-readable memory in which the data is stored. Data, in particular the virtual tomographic stroke follow-up examination image, may be provided by transmitting a signal that carries the data and/or by writing the data to a computer-readable memory and/or by displaying the data by means of a screen.

The sequence of temporally successive tomographic perfusion imaging data sets may in particular take a form such that, on the basis of the sequence of temporally successive tomographic perfusion imaging data sets, a perfusion map may be calculated. A perfusion imaging data set may include data in an image space and/or data in a projection space. Further, a perfusion imaging data set may include further data, for example acquisition protocol parameters and/or contrast agent protocol parameters of a perfusion imaging examination with which the perfusion imaging data set was captured. The sequence of temporally successive tomographic perfusion imaging data sets may for example have been captured by means of a computed tomography device and/or by means of a magnetic resonance imaging device.

A perfusion imaging data set may be in the form of a medical image, for example in the form of a two-dimensional or three-dimensional medical image. The sequence of temporally successive tomographic perfusion imaging data sets may in particular be a sequence of temporally successive tomographic medical images from a perfusion examination.

One embodiment provides for the method to further include the following step:

automatically segmenting stroke-damaged tissue in the virtual tomographic stroke follow-up examination image by applying a segmentation algorithm to the virtual tomographic stroke follow-up examination image, for example by means of a segmentation processor unit.

One embodiment provides for the trained machine learning algorithm to include an encoder network that extracts features from the sequence of temporally successive tomographic perfusion imaging data sets, and/or for the trained machine learning algorithm to include a decoder network that generates the virtual tomographic stroke follow-up examination image on the basis of the extracted features.

One embodiment provides for the encoder network to include a plurality of parallel input channels, wherein each input channel of the plurality of parallel input channels is intended for feeding a respective perfusion imaging data set to the encoder network, and/or for all the perfusion imaging data sets of the sequence of temporally successive tomographic perfusion imaging data sets to be fed to the encoder network in parallel, for example by means of the plurality of parallel input channels.

In particular, the number of input channels of the plurality of parallel input channels may be greater than or equal to the number of perfusion imaging data sets of the sequence of temporally successive tomographic perfusion imaging data sets. In particular, the encoder network for each perfusion imaging data set of the sequence of temporally successive tomographic perfusion imaging data sets may include a respective input channel.

One embodiment provides for the encoder network to include a convolution operator that is active in a temporal dimension and in a plurality of spatial dimensions.

The temporal dimension may for example refer to a temporal sequence of perfusion imaging data sets of the sequence of temporally successive tomographic perfusion imaging data sets and/or a series of input channels of the plurality of parallel input channels.

The plurality of spatial dimensions may for example refer to an image space of the perfusion imaging data sets of the sequence of temporally successive tomographic perfusion imaging data sets. The image space of the perfusion imaging data sets may be for example two-dimensional or three-dimensional. The plurality of spatial dimensions may in particular be two dimensions that relate to a two-dimensional image space, or three dimensions that relate to a three-dimensional image space.

One embodiment provides for the encoder network to include a convolutional neural network that extracts a sequence of temporally successive image space features from the sequence of temporally successive tomographic perfusion imaging data sets, and/or for the encoder network to include a recurrent neural network that determines, from the sequence of temporally successive image space features, a temporal connection between the image space features of the sequence of temporally successive image space features.

One embodiment provides for the trained machine learning algorithm to include a generator network that generates candidate images for the virtual tomographic stroke follow-up examination image on the basis of the sequence of temporally successive tomographic perfusion imaging data sets, in particular in accordance with a generative model, and for the trained machine learning algorithm to include a classifier network that evaluates the candidate images for the virtual tomographic stroke follow-up examination image, in particular in accordance with a discriminative model and/or in relation to a connection with the sequence of temporally successive tomographic perfusion imaging data sets.

In particular, the generator network and the classifier network may together carry out a zero-sum game and/or cooperate as generative adversarial networks.

According to one embodiment, the generator network includes the encoder network and/or the decoder network.

One embodiment provides for the method to further include the following steps:

receiving a set of training pairs, for example by means of a training pair receiving interface, wherein each pair of the set of training pairs includes a training sequence of temporally successive tomographic perfusion imaging data sets of the region for examination that was captured during a stroke diagnosis examination, and a tomographic training stroke follow-up examination image of the region for examination, in particular a real tomographic training stroke follow-up examination image of the region for examination, that was generated during a stroke follow-up examination, and training the machine learning algorithm on the basis of the set of training pairs, for example by means of a training unit.

The set of training pairs may for example include one or more training pairs that each include a training sequence of temporally successive tomographic perfusion imaging data sets of the region for examination that was captured during a stroke diagnosis examination, and a virtual tomographic training stroke follow-up examination image of the region for examination that was generated by a method disclosed here or another suitable method. The training sequence may be captured for example by means of a computed tomography device and/or by means of a magnetic resonance imaging device. The training stroke follow-up examination image may for example have been captured by means of a computed tomography device and/or by means of a magnetic resonance imaging device.

For example, it may be provided for the stroke follow-up examination to have been carried out no earlier than two days, in particular no earlier than three days, after the stroke diagnosis examination, and/or for the stroke follow-up examination to have been carried out no later than ten days, in particular no later than seven days, in particular no later than five days, after the stroke diagnosis examination.

One embodiment provides for the set of training pairs to include a first partial set of first training pairs, wherein for each first training pair of the first partial set of first training pairs the region for examination was not treated for the stroke between the stroke diagnosis examination and the stroke follow-up examination, and/or for the set of training pairs to include a second partial set of second training pairs, wherein for each second training pair of the second partial set of second training pairs the region for examination was treated for the stroke between the stroke diagnosis examination and the stroke follow-up examination.

The virtual tomographic stroke follow-up examination image may in particular be a first virtual tomographic stroke follow-up examination image or a second virtual tomographic stroke follow-up examination image. In particular, in addition to the virtual tomographic stroke follow-up examination image one or more further virtual tomographic stroke follow-up examination images may be calculated and/or provided.

One embodiment provides for the first virtual tomographic stroke follow-up examination image to relate to the case in which the region for examination is not treated for the stroke between the stroke diagnosis examination and the stroke follow-up examination, and for the second virtual tomographic stroke follow-up examination image to relate to the case in which the region for examination is treated for the stroke between the stroke diagnosis examination and the stroke follow-up examination.

One embodiment provides for the first virtual tomographic stroke follow-up examination image and the second virtual tomographic stroke follow-up examination image of the region for examination to be calculated by applying the trained machine learning algorithm to the sequence of temporally successive tomographic perfusion imaging data sets.

In particular, the trained machine learning algorithm may include a first trained image calculation function for calculating the first virtual tomographic stroke follow-up examination image and a second trained image calculation function for calculating the second virtual tomographic stroke follow-up examination image. The first image calculation function may be trained for example by means of the first partial set of first training pairs. The second image calculation function may be trained for example by means of the second partial set of second training pairs.

Further, at least one embodiment of the invention relates to a providing unit for providing a virtual tomographic stroke follow-up examination image, wherein the providing unit includes:

a receiving interface, intended for receiving a sequence of temporally successive tomographic perfusion imaging data sets of a region for examination, a processor unit, intended for calculating the virtual tomographic stroke follow-up examination image of the region for examination by applying a trained machine learning algorithm to the sequence of temporally successive tomographic perfusion imaging data sets, and a providing interface, intended for providing the virtual tomographic stroke follow-up examination image.

One embodiment provides a providing unit that further includes a training pair receiving interface and a training unit.

The training pair receiving interface is intended for receiving a set of training pairs, wherein each pair of the set of training pairs includes a training sequence of temporally successive tomographic perfusion imaging data sets of the region for examination that was captured during a stroke diagnosis examination, and a tomographic training stroke follow-up examination image of the region for examination, in particular a real tomographic training stroke follow-up examination image of the region for examination, that was generated during a stroke follow-up examination. The training unit is intended for training the machine learning algorithm on the basis of the set of training pairs.

A training pair may in particular be part of a training data set that, in addition to the training sequence and the training stroke follow-up examination image, includes further training data, for example one or more further medical images, in particular further stroke follow-up examination images. Further, training of the machine learning algorithm may be based on the further training data.

One embodiment provides a providing unit that is intended for performing a method according to one or more of the disclosed aspects.

Further, at least one embodiment of the invention relates to a computer program product having a computer program that may be loaded directly into a storage unit of a providing unit, having program sections in order to perform all the steps of a method according to one of the disclosed embodiments when the program sections are executed by the providing unit.

Further, at least one embodiment of the invention relates to a non-transitory computer-readable storage medium on which program sections that are readable and executable by a providing unit are stored in order to perform all the steps of the method according to one of the disclosed embodiments when the program sections are executed by the providing unit.

The computer program product may for example be a computer program or, in addition to the computer program, include at least one additional component part. The at least one additional component part of the computer program product may take the form of hardware and/or software. The computer program product may include for example a storage medium on which at least part of the computer program product is stored, and/or a key for authenticating a user of the computer program product, in particular in the form of a dongle.

The computer program product may include for example a cloud application program that is intended for distributing program sections of the computer program to different processing units, in particular different computers, of a cloud computing system, wherein each of the processing units is intended for executing one or more program sections of the computer program.

For example, the computer program product according to one of the embodiments disclosed in this application may be stored on the computer-readable medium. The computer-readable medium may be for example a memory stick, a fixed disk or another kind of data carrier.

Stroke-damaged tissue is typically less dense than intact tissue. As a result, in a computed tomography image the stroke-damaged tissue appears as a dark coloration of the region under examination. In a diffusion MRI image, the stroke-damaged tissue is identifiable because its diffusion pattern is subject to pronounced distortion.

In particular, it is possible to use a trained machine learning algorithm that has learned where and in what circumstances dark colorations of the region under examination that refer to stroke-damaged tissue are produced. Using the virtual tomographic stroke follow-up examination image, it is possible in particular to predict where dark colorations of the region under examination would occur in a real stroke follow-up examination image. Dark regions in the virtual tomographic stroke follow-up examination image then represent a prediction of possible irreversible damage in the region under examination, for example the brain.

The stroke-damaged tissue may in particular be segmented automatically in that segmentation data is calculated that refers to the stroke-damaged tissue. The algorithm for segmentation may for example be threshold-based.

Further, the automatically segmented stroke-damaged tissue may be classified automatically, for example by applying a classification algorithm and/or by means of a classification processor unit and/or by calculating classification data that refers to the stroke-damaged tissue.

The encoder network may in particular extract features that refer to a spatial property in an image space of the perfusion imaging data sets and/or a temporal connections between the perfusion imaging data sets.

The decoder network may in particular include concatenation of upsampling steps in order, from the feature vectors of the extracted features, to arrive back at the dimension of the perfusion imaging data sets. In particular, pooling indices may be transferred from the encoder network to the decoder network. On the basis of the pooling indices, the decoder network can correctly reproduce the spatial arrangement of structures in the virtual tomographic stroke follow-up examination image.

With the aid of the machine learning algorithm, for example on the basis of a DCE sequence based directly on the perfusion imaging data sets, and without an intermediate step using mathematical models, it is possible to make a prediction regarding tissue that may be dying and thus require intervention.

Machine learning algorithms, in particular machine learning algorithms based on Deep Learning, may independently extract connections that are far more extensive than manually identified features. The machine learning algorithm may utilize all the spatial and temporal information from the complete sequence in order to learn connections. An example of such connections is provided by supply through collateral vessels, oxygen demand of the tissue, pre-existing damage, the areas supplied by the arteries, and so on. On the basis of the sequence of temporally successive tomographic perfusion imaging data sets, the machine learning algorithm can thus identify substantially more complex and/or hitherto unknown connections which could not have been identified simply on the basis of conventional perfusion maps because they do not contain the appropriate information.

For example, the encoder network may be a convolutional neural network (CNN) that has the same number of input channels as the number of images of a DCE-CT/MRI image.

The filters, in particular the convolution operators, of the encoder network that were learned during training may be dimensioned for example such that they operate on all of the perfusion imaging data sets of the sequence of temporally successive tomographic perfusion imaging data sets. This makes it possible to perform simultaneous filtering using the spatial dimensions and temporal dimension of the perfusion imaging data.

The recurrent neural network may in particular include an internal memory that makes it possible to process data sets one after the other, and in so doing to learn temporal connections. For example, the image space features of the sequence of temporally successive image space features may be fed to the recurrent neural network one after the other. Combinations of a convolutional and a recurrent neural network are also used for example for the classification of videos [8].

Conventionally, within a time frame of a few days, for example three to five days, after an acute stroke diagnosed using DCE-CT/MRI, a follow-up examination is carried out, with further static image capture using CT or MRI. Typically, in a tomographic stroke follow-up examination image, the stroke-damaged tissue is very clearly visible, since it has died in the meantime and is clearly differentiated from healthy tissue by its density or signal strength. The tissue that has died appears dark in the tomographic stroke follow-up examination image, and can be clearly delimited from the healthy tissue.

Training of the machine learning algorithm on the basis of the set of training pairs may in particular be performed in the form of an end-to-end training. For example, as a result of the training, the machine learning algorithm may learn to predict, on the basis of a DCE-CT/MRI images of a stroke diagnosis examination, the associated image of a stroke follow-up examination using CT/MRI. The virtual tomographic stroke follow-up examination image may thus in particular include information of which regions in the brain can suffer irreversible damage and for example require intervention.

As the reference for the training, it is possible to use in particular the individual grey values of the pixels of the perfusion imaging data sets. Thus, it is not necessary to perform manual segmentation and/or manual annotation in the training data. The training data thus needs only to be collected, and in particular need not be manually annotated. As a result of avoiding manual annotation, a large quantity of training data can be collected relatively simply.

In a further embodiment, it is possible to use both data from patients who have undergone therapy and also data from patients who have not had any therapy (for example because therapy was not possible in a timely manner, could not be considered because of other pathological conditions, was declined, etc.) for training of the machine learning algorithm. Thus, the machine learning algorithm can learn both to predict how the follow-up image would look with therapy and how it would look without therapy. By comparing these two predictions, valuable information for deciding on therapy can be obtained.

For this, enough training data would be needed for cases in which a stroke had been treated and in which a follow-up examination using a CT/MRI image had subsequently been carried out. In that case, it would be possible to calculate predictions of the effects of the stroke with and without treatment, which would produce a concrete decision-making aid. According to one embodiment, in the second partial set of second training pairs, a plurality of groups of second training pairs is formed that differ from one another in respect of the treatment method with which the region under examination was treated for the stroke. In that case, predictions could be calculated of the outcome of the stroke with and without treatment, depending on a treatment method.

According to one embodiment, a chance of success of a treatment of the region under examination for the stroke, in particular depending on a treatment method, is calculated and for example output in the form of a percentage figure. The chance of success may for example be calculated by applying the trained machine learning algorithm to the sequence of temporally successive tomographic perfusion imaging data sets. As an alternative or in addition to the sequence of temporally successive tomographic perfusion imaging data sets, further data, in particular patient-specific data, such as age and/or sex of the patient, may be used for calculating the chance of success.

Thus, in particular a medical imaging device is disclosed, including a providing unit for providing a virtual tomographic stroke follow-up examination image, wherein the providing unit takes a form according to one or more of the disclosed aspects. The medical imaging device may for example be a computed tomography device or a magnetic resonance imaging device.

The virtual tomographic stroke follow-up examination image may be for example a virtual computed-tomography stroke follow-up examination image or a virtual magnetic resonance imaging stroke follow-up examination image.

At least one embodiment of the invention makes it possible to interpret the result of perfusion imaging simply and unambiguously, in particular independently of a mathematical model for calculating the perfusion parameters. The automatic feature extraction using the machine learning algorithm makes it possible to identify both spatial and temporal connections in the sequence of temporally successive tomographic perfusion imaging data sets. Using the solution according to the invention, it is possible to make very precise predictions of the effect of a stroke on tissue. Moreover, the invention makes it possible to predict the success of a treatment and thus to provide a rapid and reliable decision-making aid.

In the context of this application, the term "machine learning algorithm" is understood to mean in particular an algorithm that is intended for machine learning. The machine learning algorithm may for example be intended for monitored learning and/or unmonitored learning. The machine learning algorithm may for example be intended for deep learning and/or for reinforcement learning and/or for marginal space learning.

The machine learning algorithm may be based for example on decision trees, a random forest, a logistical regression, a support vector machine, an artificial neutral network, in particular a convolutional neural network, and/or a recurrent neural network, a kernel method, Bayes classifiers or the like, or on combinations thereof.

Calculations, in particular during training of a machine learning algorithm, can be performed for example by means of a processor system. The processor system may include for example one or more processors, in particular graphic processors.

The providing unit may include for example one or more components in the form of hardware and/or one or more components in the form of software. The providing unit may be formed for example at least partly by a cloud computing system. The providing unit may be and/or include for example a cloud computing system, a computer network, a computer, a tablet computer, a smartphone or the like, or a combination thereof.

The hardware may for example cooperate with software and/or be configurable by means of software. The software may for example be executed by means of the hardware. The hardware may be for example a storage system, an FPGA (field-programmable gate array) system, an ASIC (application-specific integrated circuit) system, a microcontroller system, a processor system and combinations thereof. The processor system may for example include a microprocessor and/or a plurality of cooperating microprocessors.

In particular, a component of the providing unit according to one or more of the aspects disclosed in this application, which is intended for carrying out a given step of a method according to one or more of the aspects disclosed in this application, may be implemented in the form of hardware that is configured for carrying out the given step and/or that is configured for executing a computer-readable instruction such that the hardware is configurable by means of the computer-readable instruction for carrying out the given step. The steps of the method may be carried out for example in a processor, in particular in the form of calculations. In particular, the providing unit may include a memory region, for example in the form of a computer-readable medium, in which there are stored computer-readable instructions, for example in the form of a computer program.

A data transfer between components of the providing unit may for example be performed in each case by means of a suitable data transfer interface. The data transfer interface for the transfer of data to and/or from a component of the providing unit may be realized at least partly in the form of software and/or at least partly in the form of hardware. The data transfer interface may for example be intended for storing data in and/or for loading data from a region of the storage system, wherein one or more components of the providing unit may access this region of the storage system.

Within the context of embodiments of the invention, features that have been described with reference to different embodiments of the invention and/or different categories of claim (method, use, device, system, arrangement, etc.) may be combined to form further embodiments of the invention. For example, a claim that relates to a device may also be developed using features that are described or claimed in conjunction with a method, and vice versa. Here, functional features of a method may be carried out by correspondingly formed concrete components. In addition to the embodiments of the invention that are explicitly described in this application, diverse further embodiments of the invention are conceivable that those skilled in the art may arrive at without departing from the scope of the invention predetermined by the claims.

The use of the indefinite articles "a" or "an" does not rule out the possibility that the feature concerned may also be present a plurality of times. The use of the term "include" does not rule out the possibility that the terms linked by means of the term "include" are identical. For example, the providing unit includes the providing unit. The use of the term "unit" does not rule out the possibility that the object to which the term "unit" refers may include a plurality of components that are spatially separated from one another.

The term "on the basis of" may, in the context of the present application, be understood in particular in the sense of the term "using". In particular, a formulation in accordance with which a first feature is generated (or alternatively, is produced, determined, etc.) on the basis of a second feature does not rule out the possibility that the first feature may be generated (or alternatively, may be produced, determined, etc.) on the basis of a third feature.

FIG. 1 shows a flow chart for a method for providing a virtual tomographic stroke follow-up examination image, wherein the method includes the following steps:

receiving RS a sequence of temporally successive tomographic perfusion imaging data sets of a region for examination, calculating CI the virtual tomographic stroke follow-up examination image of the region for examination by applying a trained machine learning algorithm to the sequence of temporally successive tomographic perfusion imaging data sets, and providing PI the virtual tomographic stroke follow-up examination image.

Figure 2:
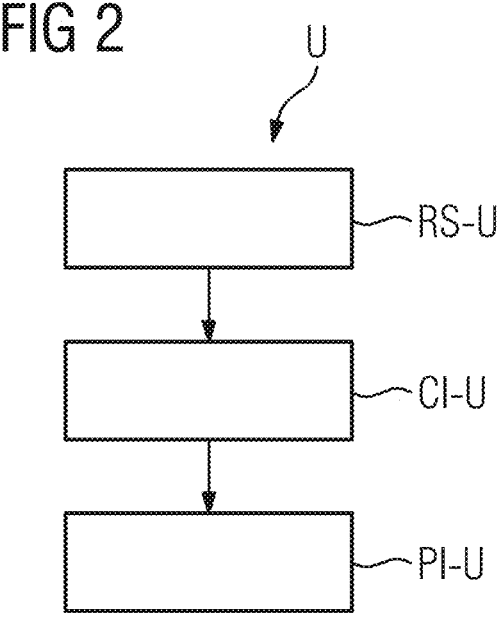
FIG. 2 shows a providing unit for providing a virtual tomographic stroke follow-up examination image.

FIG. 2 shows a providing unit U for providing a virtual tomographic stroke follow-up examination image, including:

a receiving interface RS-U, intended for receiving RS a sequence of temporally successive tomographic perfusion imaging data sets of a region for examination, a processor unit CI-U, intended for calculating CI the virtual tomographic stroke follow-up examination image of the region for examination by applying a trained machine learning algorithm to the sequence of temporally successive tomographic perfusion imaging data sets, and a providing interface PI-U, intended for providing PI the virtual tomographic stroke follow-up examination image.

Figure 3:
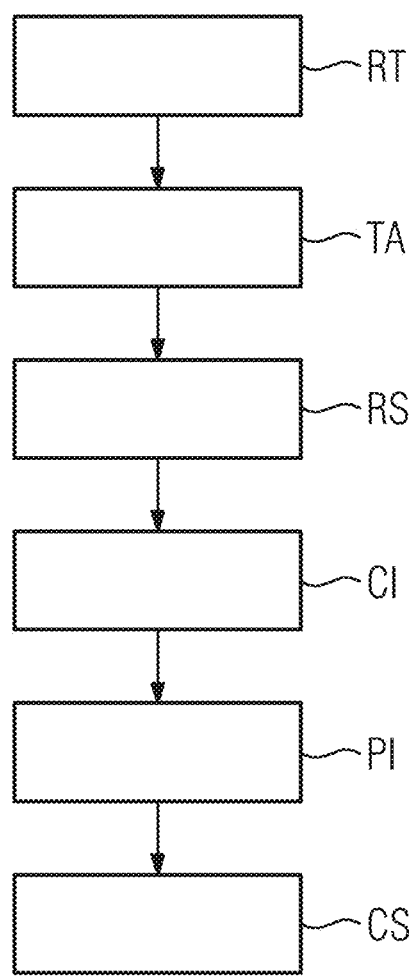
FIG. 3 shows a flow chart for a method for providing a virtual tomographic stroke follow-up examination image, in which a machine learning algorithm is trained.

FIG. 3 shows a flow chart for a method for providing a virtual tomographic stroke follow-up examination image, wherein the method further includes the following steps:

receiving RT a set of training pairs, wherein each pair of the set of training pairs includes a training sequence of temporally successive tomographic perfusion imaging data sets of the region for examination that was captured during a stroke diagnosis examination, and a tomographic training stroke follow-up examination image of the region for examination that was generated during a stroke follow-up examination, training TA the machine learning algorithm on the basis of the set of training pairs, and automatically segmenting CS stroke-damaged tissue in the virtual tomographic stroke follow-up examination image by applying a segmentation algorithm to the virtual tomographic stroke follow-up examination image.

Figure 4:
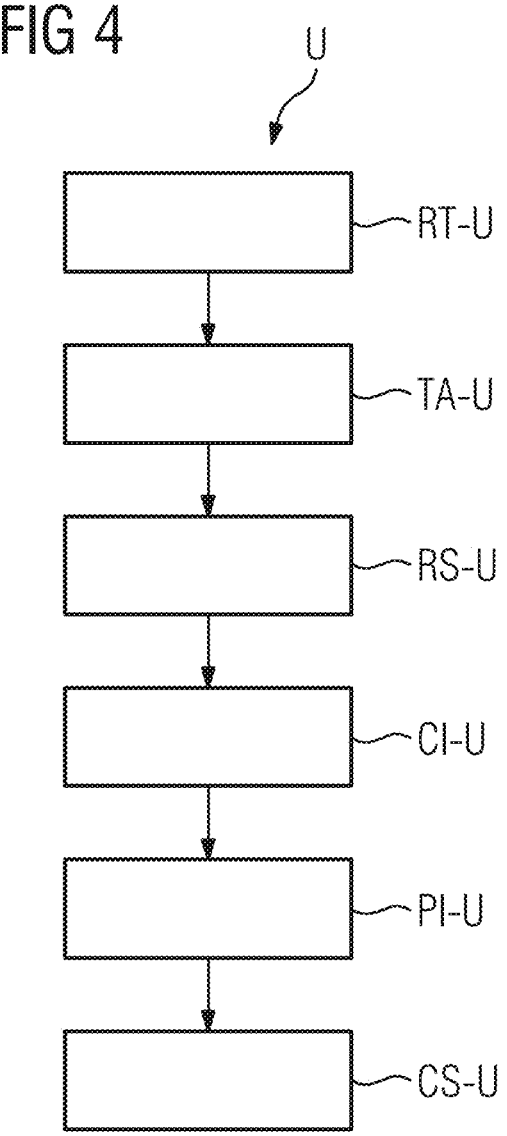
FIG. 4 shows a providing unit for providing a virtual tomographic stroke follow-up examination image including a training unit for training the machine learning algorithm.

FIG. 4 shows a providing unit U for providing a virtual tomographic stroke follow-up examination image, further including:

a training pair receiving interface RT-U, intended for receiving RT a set of training pairs, wherein each pair of the set of training pairs includes a training sequence of temporally successive tomographic perfusion imaging data sets of the region for examination that was captured during a stroke diagnosis examination, and a tomographic training stroke follow-up examination image of the region for examination that was generated during a stroke follow-up examination, a training unit TA-U, intended for training TA the machine learning algorithm on the basis of the set of training pairs, a segmentation processor unit CS-U, for automatically segmenting CS stroke-damaged tissue in the virtual tomographic stroke follow-up examination image by applying a segmentation algorithm to the virtual tomographic stroke follow-up examination image.

Figure 5:
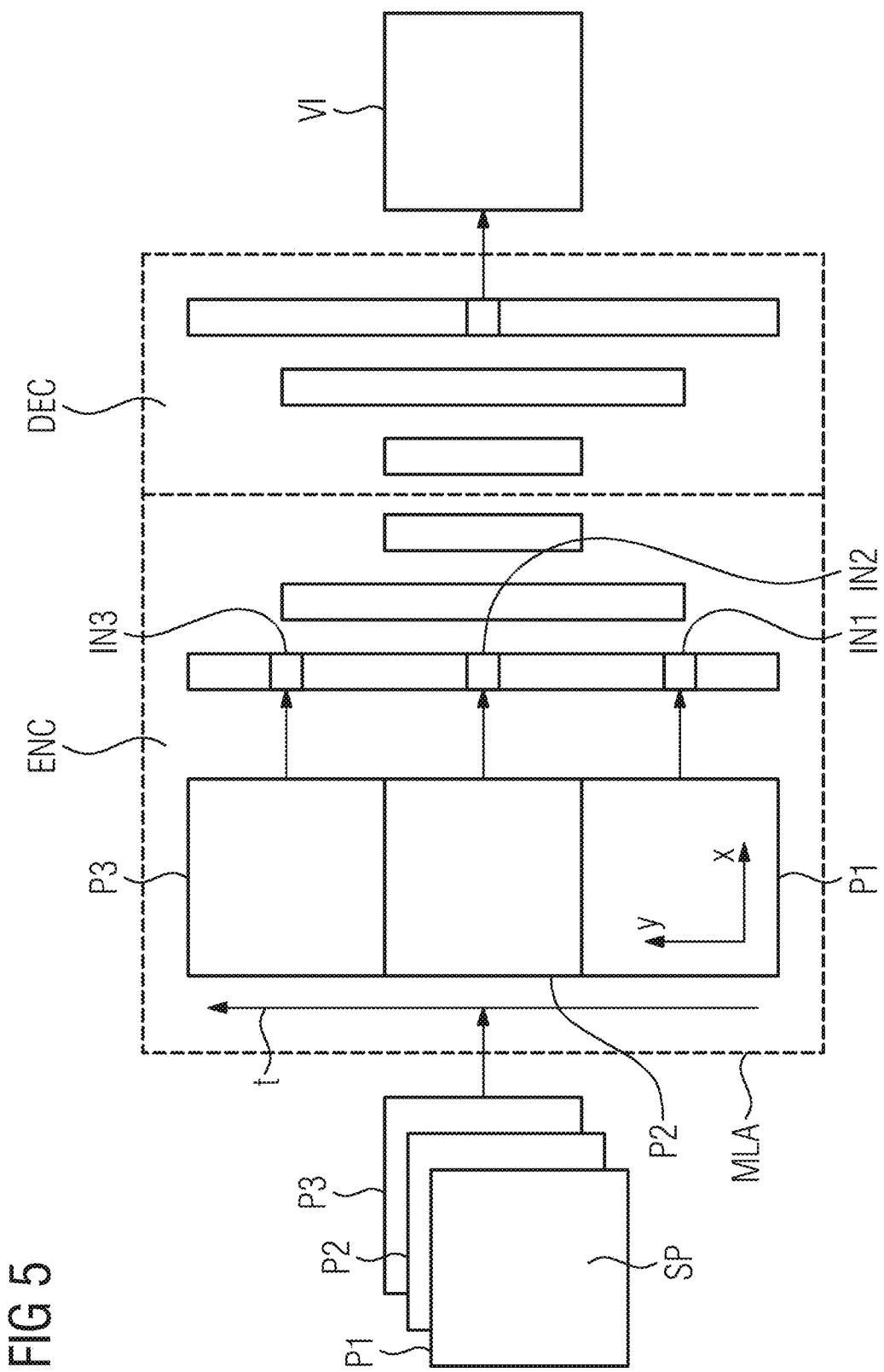
FIG. 5 shows a data flow for a machine learning algorithm having an encoder network that includes a plurality of parallel input channels.

FIG. 5 shows a data flow for a machine learning algorithm MLA having an encoder network ENC that includes a plurality of parallel input channels IN1, IN2, IN3. The trained machine learning algorithm MLA further includes a decoder network DEC which, on the basis of the extracted features, generates the virtual tomographic stroke follow-up examination image VI.

Each input channel of the plurality of parallel input channels IN1, IN2, IN3 is intended for feeding a respective perfusion imaging data set P1, P2, P3 to the encoder network ENC. All the perfusion imaging data sets P1, P2, P3 of the sequence SP of temporally successive tomographic perfusion imaging data sets P1, P2, P3 are fed to the encoder network ENC in parallel. The encoder network ENC includes a convolution operator that is active in a temporal dimension t and a plurality of spatial dimensions x, y.

Figure 6:
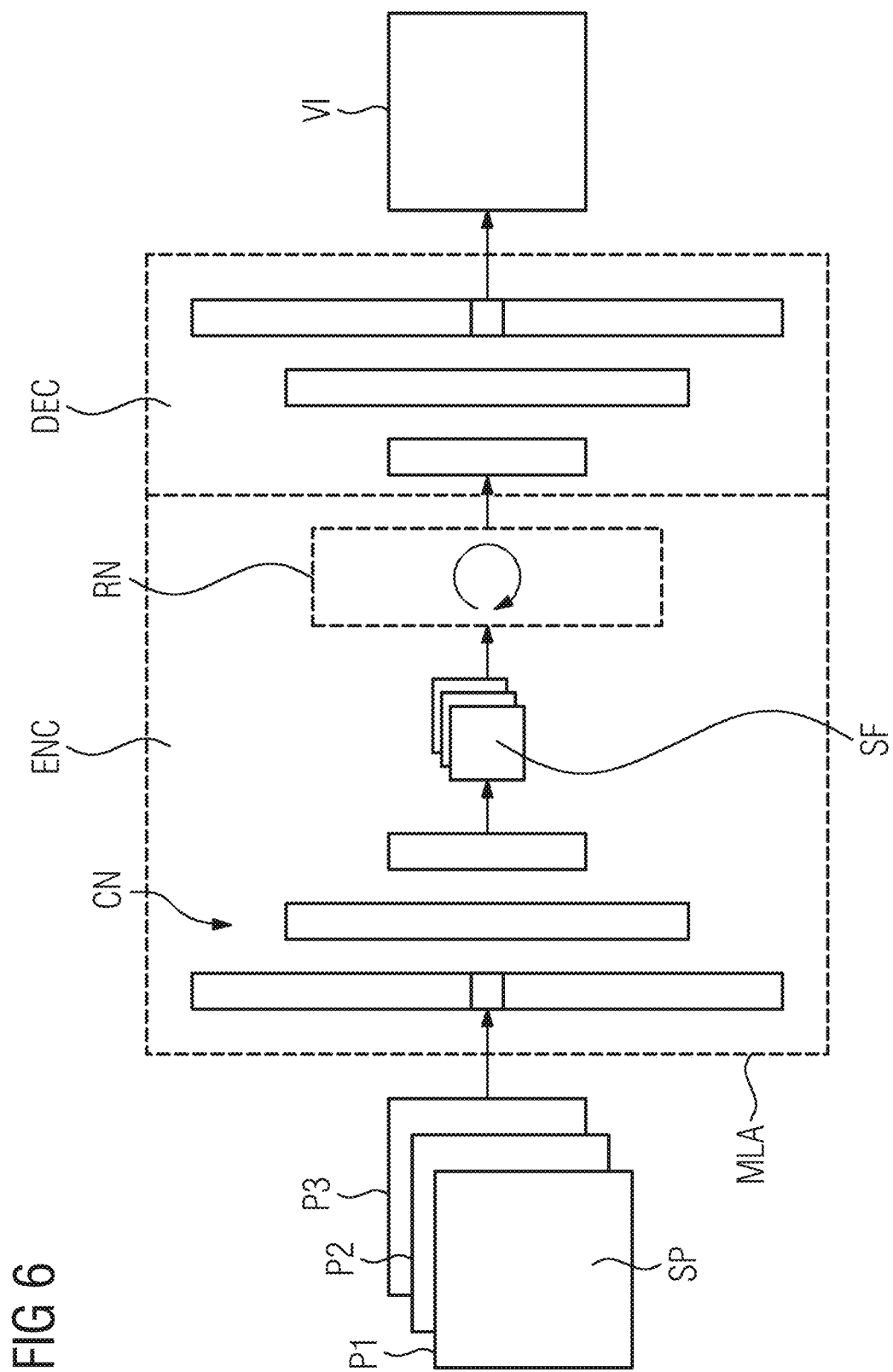
FIG. 6 shows a data flow for a machine learning algorithm having an encoder network that includes a recurrent neural network.

FIG. 6 shows a data flow for a machine learning algorithm MLA having an encoder network ENC that includes a recurrent neural network RN and a convolutional neural network CN. The convolutional neural network CN extracts, from the sequence SP of temporally successive tomographic perfusion imaging data sets P1, P2, P3, a sequence SF of temporally successive image space features. The recurrent neural network determines, from the sequence SF of temporally successive image space features, a temporal connection between the image space features of the sequence SF of temporally successive image space features. On the basis of the sequence SF of temporally successive image space features and the temporal connection between the image space features of the sequence SF of temporally successive image space features, the decoder network DEC generates the virtual tomographic stroke follow-up examination image VI.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LITERATURE REFERENCES

[1] C. Cuenod and D. Balvay, "Perfusion and vascular permeability: Basic concepts and measurement in DCE-CT and DCE-MRI", Diagnostic and Interventional Imaging, 2013.
[2] C. Roberts, B. Issa, A. Stone, A. Jackson, J. C. Waterton and G. J. M. Parker, "Comparative Study into the Robustness of Compartmental Modeling and Model-Free Analysis in DCE-MRI Studies", JOURNAL OF MAGNETIC RESONANCE IMAGING, 2006.
[3] T. Hachaj and R. M. Ogiela, "Neural Network Approach for Identification of Selected Brain Perfusion Abnormalities: neural net on perfusion map", in 6th International Conference on Innovative Mobile and Internet Services in Ubiquitous Computing, 2012.
[4] T. Hachaja and M. R. Ogiela, "Application of neural networks in detection of abnormal brain perfusion regions", Neurocomputing, 2013.
[5] F. Flottmann, G. Broocks, T. D. Faizy, M. Ernst, N. D. Forkert, M. Grosser, G. Thomalla, S. Siemonsen, J. Fiehler and A. Kemmling, "CT-perfusion stroke imaging: a threshold free probabilistic approach to predict infarct volume compared to traditional ischemic thresholds", Nature: Scientific Reports, 2017.
[6] R. Grech, P. L. Galvin, S. Power, A. O'Hare, S. Looby, P. Brennan and J. Thornton, "Outcome Prediction in Acute Stroke Patients Considered for Endovascular Treatment: a Novel Tool", Intery Neuroradiol., 2014.
[7] I. Rekik, S. Allassonnière, T. K. Carpenter and J. M. Wardlaw, "Medical image analysis methods in MR/CT-imaged acute-subacute ischemic stroke lesion: Segmentation, prediction and insights into dynamic evolution simulation models. A critical appraisal", NeuroImage: Clinical, 2012.
[8] D. Graham, S. H. F. Langroudi, C. Kanan and D. Kudithipudi, "Convolutional Drift Networks for Video Classification", IEEE Rebooting Computing, 2017.

What is claimed is:

1. A method for providing a virtual tomographic stroke follow-up examination image, the method comprising:
receiving a sequence of temporally successive tomographic perfusion imaging data sets of a region for examination;
calculating the virtual tomographic stroke follow-up examination image of the region for examination by applying a trained machine learning algorithm to the sequence of temporally successive tomographic perfusion imaging data sets received; and
providing the virtual tomographic stroke follow-up examination image calculated.

2. The method of claim 1, further comprising:
automatically segmenting stroke-damaged tissue in the virtual tomographic stroke follow-up examination image by applying a segmentation algorithm to the virtual tomographic stroke follow-up examination image.

3. The method of claim 1,
wherein the trained machine learning algorithm includes an encoder network to extract features from the sequence of temporally successive tomographic perfusion imaging data sets, and
wherein the trained machine learning algorithm includes a decoder network to generate the virtual tomographic stroke follow-up examination image based upon the features extracted.

4. The method of claim 3,
wherein the encoder network includes a plurality of parallel input channels, wherein each input channel of the plurality of parallel input channels is intended for feeding a respective perfusion imaging data set, of the sequence of temporally successive tomographic perfusion imaging data sets, to the encoder network, and
wherein a plurality of perfusion imaging data sets of the sequence of temporally successive tomographic perfusion imaging data sets are fed by the plurality of parallel input channels to the encoder network in parallel.

5. The method of claim 4,
wherein the encoder network includes a convolution operator that is active in a temporal dimension and in a plurality of spatial dimensions.

6. The method of claim 3,
wherein the encoder network includes a convolutional neural network to extract a sequence of temporally successive image space features from the sequence of temporally successive tomographic perfusion imaging data sets, and
wherein the encoder network includes a recurrent neural network to determine, from the sequence of temporally successive image space features, a temporal connection between the image space features of the sequence of temporally successive image space features.

7. The method of claim 1,
wherein the trained machine learning algorithm includes a generator network to generate candidate images for the virtual tomographic stroke follow-up examination image based upon the sequence of temporally successive tomographic perfusion imaging data sets, and
wherein the trained machine learning algorithm includes a classifier network to evaluate the candidate images for the virtual tomographic stroke follow-up examination image.

8. The method of claim 1, wherein the method further includes:
receiving a set of training pairs, wherein each pair of the set of training pairs includes a training sequence of temporally successive tomographic perfusion imaging data sets of the region for examination that was captured during a stroke diagnosis examination, and a tomographic stroke follow-up examination image of the region for examination that was generated during a stroke follow-up examination, and
training the machine learning algorithm based upon the set of training pairs.

9. The method of claim 8,
wherein the set of training pairs includes a first partial set of first training pairs, wherein for each first training pair of the first partial set of first training pairs the region for examination was not treated for the stroke between the stroke diagnosis examination and the stroke follow-up examination, and
wherein the set of training pairs includes a second partial set of second training pairs, wherein for each second training pair of the second partial set of second training pairs the region for examination was treated for the stroke between the stroke diagnosis examination and the stroke follow-up examination.

10. The method of claim 8,
wherein a first virtual tomographic stroke follow-up examination image and a second virtual tomographic stroke follow-up examination image of the region for examination are calculated by applying the trained machine learning algorithm to the sequence of temporally successive tomographic perfusion imaging data sets,
wherein the first virtual tomographic stroke follow-up examination image relates to the region for examination not being treated for the stroke between the stroke diagnosis examination and the stroke follow-up examination, and
wherein the second virtual tomographic stroke follow-up examination image relates to the region for examination being treated for the stroke between the stroke diagnosis examination and the stroke follow-up examination.

11. A providing unit for providing a virtual tomographic stroke follow-up examination image, comprising:
a receiving interface, to receive a sequence of temporally successive tomographic perfusion imaging data sets of a region for examination;
a processor, to calculate the virtual tomographic stroke follow-up examination image of the region for examination by applying a trained machine learning algorithm to the sequence of temporally successive tomographic perfusion imaging data sets received; and
a providing interface, to provide the virtual tomographic stroke follow-up examination image calculated.

12. The providing unit of claim 11, further comprising:
a training pair receiving interface, to receive a set of training pairs, wherein each pair of the set of training pairs includes a training sequence of temporally successive tomographic perfusion imaging data sets of the region for examination that was captured during a stroke diagnosis examination, and a tomographic training stroke follow-up examination image of the region for examination that was generated during a stroke follow-up examination, and
a training unit, to train the machine learning algorithm based upon the set of training pairs received.

13. A non-transitory computer program product, storing a computer program, directly loadable into a storage unit of a providing unit, including program sections to perform the method of claim 1 when the program sections are executed by the providing unit.

14. A non-transitory computer-readable storage medium storing program sections, readable and executable by a providing unit, to perform the method of claim 1 when the program sections are executed by the providing unit.

15. The method of claim 2,
wherein the trained machine learning algorithm includes an encoder network to extract features from the sequence of temporally successive tomographic perfusion imaging data sets, and
wherein the trained machine learning algorithm includes a decoder network to generate the virtual tomographic stroke follow-up examination image based upon the features extracted.

16. The method of claim 15,
wherein the encoder network includes a plurality of parallel input channels, wherein each input channel of the plurality of parallel input channels is intended for feeding a respective perfusion imaging data set, of the sequence of temporally successive tomographic perfusion imaging data sets, to the encoder network, and
wherein a plurality of perfusion imaging data sets of the sequence of temporally successive tomographic perfusion imaging data sets are fed by the plurality of parallel input channels to the encoder network in parallel.

17. The method of claim 16,
wherein the encoder network includes a convolution operator that is active in a temporal dimension and in a plurality of spatial dimensions.

18. The method of claim 15,
wherein the encoder network includes a convolutional neural network to extract a sequence of temporally successive image space features from the sequence of temporally successive tomographic perfusion imaging data sets, and
wherein the encoder network includes a recurrent neural network to determine, from the sequence of temporally successive image space features, a temporal connection between the image space features of the sequence of temporally successive image space features.

19. A non-transitory computer program product, storing a computer program, directly loadable into a storage unit of a providing unit, including program sections to perform the method of claim 2 when the program sections are executed by the providing unit.

20. A non-transitory computer-readable storage medium storing program sections, readable and executable by a providing unit, to perform the method of claim 2 when the program sections are executed by the providing unit.

* * * * *